United States Patent [19]
Blake et al.

[11] Patent Number: 6,103,944
[45] Date of Patent: *Aug. 15, 2000

[54] WATER SEPARATION PROCESS

[75] Inventors: Charles Brian Blake, Chester; James Malcolm Forsyth, Manchester; Ann San Liow, Runcorn; Stephen John Adams, Warrington; Ralph Jones Doy; Rowland John Porter Brierley, both of Cleveland; Jane Andrea Eileen Roberts, Chester; Brian Schofield, Atherton; Neil David Shilling, Northwich, all of United Kingdom

[73] Assignee: Imperial Chemical Industries PLC, London, United Kingdom

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/235,927

[22] Filed: May 2, 1994

Related U.S. Application Data

[62] Division of application No. 07/987,718, Dec. 9, 1992, Pat. No. 5,334,784.

[30]  Foreign Application Priority Data

| Dec. 10, 1991 | [GB] | United Kingdom | 9126228 |
| Sep. 3, 1992 | [GB] | United Kingdom | 9218607 |
| Sep. 15, 1992 | [GB] | United Kingdom | 9219469 |

[51] Int. Cl.$^7$ .......................... C01C 17/08; C01C 19/08; B01D 53/14
[52] U.S. Cl. ..................... 570/165; 570/165; 570/166; 570/167; 570/168; 570/169; 570/177; 423/240 R; 423/488; 423/241; 95/231; 502/514
[58] Field of Search ................................. 423/488, 241, 423/240 R; 95/231, 233; 570/165, 166, 167, 168, 169, 177; 502/514

[56] References Cited

U.S. PATENT DOCUMENTS

| 3,218,364 | 11/1965 | Kometani et al. | 570/177 |
| 3,300,538 | 1/1967 | Kometani et al. | 570/177 |
| 3,725,536 | 4/1973 | Gentili | 95/233 |
| 3,792,104 | 2/1974 | Mueller | 585/609 |
| 3,855,399 | 12/1974 | van Eiji | 423/488 |
| 3,919,399 | 11/1975 | Schabacher et al. | 423/488 |
| 4,150,102 | 4/1979 | Schabacher et al. | 423/488 |
| 5,171,899 | 12/1992 | Furutaka et al. | 570/164 |
| 5,208,398 | 5/1993 | Wismer | 570/177 |
| 5,243,105 | 9/1993 | Scott et al. | 570/165 |

FOREIGN PATENT DOCUMENTS

| 0283965 | 9/1988 | European Pat. Off. . |
| 0449617 | 10/1991 | European Pat. Off. . |
| 2099786 | 3/1972 | France . |

*Primary Examiner*—Ngoc-Yen Nguyen
*Attorney, Agent, or Firm*—Pillsbury Madison & Sutro LLP

[57]  ABSTRACT

Water present in a hot gaseous product stream from a reactor system A.B (FIG. 1) containing hydrogen fluoride is separated from the stream in order to eliminate a potentially corrosive combination of water and HF. The water is removed by contacting the gaseous product stream with liquid HF in a distillation column so as to obtain a bottoms product containing liquid HF and water and a top product containing dry HF and the product to be recovered. The invention encompasses the separation process, a vessel for carrying out the process (FIGS. 2 to 4), a control system for the liquid HF supply to the distillation column (FIGS. 5 and 6) and a recovery system for recovering HF employed during operation of the reactor system in different regimes employing HF as a fluorination agent, as a diluent during catalyst regeneration and/or catalyst prefluorination (FIG. 7).

14 Claims, 5 Drawing Sheets

WATER SEPARATION PROCESS

This is a division of application Ser. No. 07/987,718, filed Dec. 9, 1992, now U.S. Pat. No. 5,334,784.

This invention relates to a process involving the treatment of water-containing gaseous streams.

In particular, the invention relates to a process involving a gaseous stream containing hydrogen fluoride and water vapour.

BACKGROUND OF THE INVENTION

A typical process to which the invention pertains is the reaction of hydrogen fluoride with various compounds, for example chlorinated alkanes or chlorinated olefins, over catalysts such as chromium oxide for the purpose of effecting fluorination of such compounds. For instance, $C_2$ compounds such as trichloroethylene and/or 1,1,1-trifluoro-2-chloroethane may be fluorinated to produce 1,1,1,2-tetrafluoroethane (Refrigerant 134a).

A typical gaseous product stream obtained in these processes can contain fluorinated product, unchanged starting material, unchanged HF, and HCl as a product of the halogen exchange reaction. We have found that, in scaling up such fluorination processes with the aim of achieving acceptable conversion efficiencies, the gaseous product stream may contain unacceptable levels of water vapour. For instance, in the reaction of trichloroethylene and/or 1,1,1-trifluoro-2-chloroethane with HF to produce 1,1,1,2-tetrafluoroethane, conversion efficiency may be enhanced by carrying out the process using a stoichiometric excess of HF and an increased inventory of catalyst. However, any water that may be generated in the course of carrying out the reaction (eg removal of oxygen from the catalyst which will often be an oxide) or present in the reactants, will tend combine with the HF because of the affinity of HF for water and, if the HF is recycled to the reaction as is desirable if effective use is to be made of the HF, the water content in the gaseous product stream tends to build up. The presence of significant amounts of water in the gaseous product stream gives rise to a serious obstacle to further treatment of this reaction stream because of the highly corrosive nature of condensate containing HF and water. It is well known that aqueous solutions of HF attack all normal materials of construction; consequently, unless the problem posed by the increased water content resulting from operation with an excess of HF and increased inventory of catalyst can be overcome, the opportunities for enhanced conversion efficiency afforded by these expedients are largely counteracted by the need to employ expensive HF-resistant coatings for ductwork/vessels etc in the further stages of the process.

SUMMARY OF THE INVENTION

According to a first broad aspect of the invention there is provided a process of treating a gaseous stream containing water, comprising contacting the gaseous stream with liquid HF to effect mass transfer of water from the gaseous stream to the liquid HF.

More specifically the invention is concerned with treatment of a gaseous stream containing HF and water.

According to a second aspect of the present invention there is provided a process for effecting fluorination of a compound comprising the gaseous phase reaction of the compound with HF in the presence of a fluorination catalyst, characterised by at least partially removing any water present in the gaseous product stream derived from the reaction by contacting the gaseous product stream with liquid HF.

The invention has particular application when the reaction is carried out with HF in stoichiometric excess; and even more so when HF in the gaseous product stream is recycled to the reaction.

The compound may comprise trichloroethylene and/or 1,1,1-trifluorochloroethane. Where the reaction is between trichloroethylene and HF, the quantity of HF employed may be from 10 to 100, preferably 15 to 60, moles of HF per mole of trichloroethylene. Where the reaction involves fluorination of 1,1,1-trifluoro-2-chloroethane, the amount of HF may be up to 10 moles, and preferably from 2 to 6 moles, of HF per mole of 1,1,1-trifluoro-2-chloroethane.

Typically, the fluorination catalyst comprises any of the fluorination catalysts described in the prior art including various inorganic compounds, for example oxides, halides and oxyhalides of metals such as aluminium, cobalt, manganese, iron and especially chromium. A preferred catalyst is chromia or a zinc or nickel promoted chromia.

According to a third aspect of the present invention there is provided a process for the manufacture of 1,1,1,2-tetrafluoroethane, comprising:

(a) effecting the gaseous phase reaction of trichloroethylene and/or 1,1,1-trifluoro-2-chloroethane with a stoichiometric excess of HF in the presence of a fluorination catalyst;

(b) contacting the resulting gaseous product stream with liquid HF to effect mass transfer of water present in the gaseous product stream to said liquid HF; and (c) recycling HF obtained from said product stream following step (b) to the reaction of step (a).

DETAILED DESCRIPTION OF THE INVENTION

The process for the manufacture of 1,1,1,2-tetrafluoroethane may be carried out in accordance with the reaction sequence described and claimed in our prior published European Patent Application No. 449617.

Usually, prior to contact with the liquid HF, the gaseous product stream will be at a temperature above the dew point of the HF/water component of the product. Typically, the temperature of the gaseous product stream will be between 150 and 300° C. prior to such contact.

The HF and water content in the gaseous product stream, expressed as a percentage by weight of the total product stream, is typically up to about 35 wt % in the case of HF and up to about 0.15 wt % in the case of water.

At least part of the HF used in the fluorination step of said second or third aspect of the invention may be derived from HF/moisture containing off-gases produced in the course of conditioning/regeneration of a fluorination catalyst carried out simultaneously with said fluorination process. For instance, conditioning of the catalyst may be carried out by passing substantially dry HF with or without nitrogen diluent over the catalyst at about 250 to 450° C. whilst regeneration of the catalyst may be carried out using a mixture of substantially dry HF and an oxidising gas such as air or oxygen, at a temperature in the range of 300 to 500° C. as disclosed in our prior EP-A-475693.

For example, in one embodiment of the invention, plant for carrying out the fluorination process comprises first and second reactor means each operable in a first mode for effecting fluorination of said compound(s) by gaseous phase reaction of said compound(s) with HF in the presence of a fluorination catalyst, each of said first and second reactor means being operable in a second mode in which the fluorination catalyst is conditioned/regenerated in a process resulting in off-gases containing HF and moisture; means downstream of said first and second reactor means for effecting processing of the product streams produced thereby, said downstream means including means for contacting the resulting gaseous product stream from said first mode operation of the reactor means with liquid HF to effect mass transfer of water present in the gaseous product stream to said liquid HF and means for recycling at least HF derived from said gaseous product stream to the reactor means operating in said first mode; means for alternating operation of said first and second reactor means such that one of said reactor means is operated in its first mode while the other is operated in its second mode and vice versa; and means for supplying the off-gases derived from the reactor means operating in said second mode to the downstream means whereby HF derived from said other reactor means is recycled to the reactor means operating in said first mode.

Thus, the wet HF, which is derived from the catalyst conditioning/regeneration process carried out in one of said reactor means and which will generally be at an elevated temperature and hence of a corrosive nature, is used as a source of the HF reactant for the fluorination process carried out in the other reactor means. Thus, whilst at face value it would appear undesirable to deliberately allow the introduction of water into the fluorination process because of the problems that arise in the downstream processing of a product stream containing HF and water, the present invention permits this by including in the downstream processing means said means for contacting the product stream with liquid HF. The introduction of wet HF into the fluorination process rather than subjecting it to a scrubbing operation, enables more efficient use of the HF and also avoids problems that would otherwise arise in providing pressure isolation between the conditioning/regeneration process, involving high pressures, and a scrubbing process at low pressure.

Where used in the production of 1,1,1,2-tetrafluoroethane, each of the reactor means may comprise two stages as disclosed in our prior European Patent Application No.449617. In this event, the HF/moisture containing off-gases derived from the reactor means operating in said second mode may be added to the product stream resulting from step (B) as disclosed in EP-A-449617.

It will be understood that, in use, the liquid HF may contain other components such as water and reaction products derived from the gaseous product stream. At start-up of the process, the liquid may comprise substantially pure HF.

Preferably, in each of the aspects referred to above, contact between the gaseous stream and the liquid HF is effected in a distillation zone with the gaseous stream at an elevated temperature and pressure so that HF and the product or products of the reaction are distilled from the water. For instance, in the third aspect of the invention, the distillate typically comprises substantially dry HF and organics resulting from the reaction and the water is absorbed into the liquid HF which may be withdrawn from the distillation zone so that separation of water from the HF can be carried out, eg in a suitable still. The distillate is withdrawn for further processing, eg to separate HF and organic components from the product stream derived from the fluorination reaction.

The elevated temperature of the gaseous stream is preferably such that distillation can be effected without a reboiler, ie the reboil heat input to the distillation zone is provided by the gaseous stream.

The water content in the gaseous product stream may be derived from one or more sources, such as: water present in one or more of the reactants; water occluded or otherwise present in the catalyst; water produced as a result of interaction between one or more of the reactants and the catalyst (either fresh or regenerated); water produced during conditioning/regeneration of the catalyst; or water contained in any other medium introduced in the course of the reaction. Typically the water content in the gaseous product stream will be at least 200 ppm (relative to the HF in the product stream) and may range up to about 6000 ppm depending, inter alia, on the condition of the catalyst.

Where contact between the gaseous product stream and liquid HF is carried out in a distillation zone, the gaseous stream may be introduced into the liquid HF at a point beneath the liquid level thereof so as to effect de-superheating of the incoming gaseous product stream. Alternatively or additionally, the gaseous stream or a fraction thereof may be introduced into the distillation zone at a point above the liquid level. The distillation zone may include a series of trays disposed in vertically spaced relation such that liquid HF (together with some organics) collects on the trays in the course of the distillation process for contact with the gaseous stream. In the latter case, part of the distillation zone may constitute means for de-superheating the gaseous product stream; for example, one or more trays in the vicinity of the point of introduction of the gaseous product stream into the distillation zone may form a de-superheating section where contact between the gaseous product stream and the liquid HF serves to effect a substantial reduction in the temperature of the incoming gaseous product stream.

Where distillation is carried out in a column in which the superheat of the product stream is removed by contact of the product stream with liquid HF in a trayed section of the distillation column, the materials of construction will be protected from corrosion by the HF/water component of the gaseous product stream. By removing the superheat in this manner rather than introducing the product stream into liquid HF below the liquid level thereof, it is possible to operate the column with a comparatively small inventory of liquid HF, which is advantageous from a safety standpoint. Removal of the superheat by introduction of the product stream into a substantial bulk of liquid HF has the advantage that, if the bulk of liquid HF is large, the temperature of the product stream may be reduced below the dew point of the HF/water (at which the HF/water is at its most corrosive level) thus permitting the column to be constructed from less expensive materials. However, in this event, a considerably larger inventory of liquid HF is required within the distillation column compared with that required when the superheat is removed in said trayed section.

In one embodiment of the invention, a gaseous mixture at 200° C. containing HF, up to 6000 ppm water (relative to the HF) and various chlorinated and fluorinated $C_2$ compounds is introduced into HF liquid, at a point below the liquid level, in a distillation zone under a pressure of 13 bar absolute. Under these conditions, the liquid HF has a boiling point of about 100° C. The gaseous mixture, cooled to 120° C., is then passed through a condenser to give substantially dry HF as distillate, the organic materials being subjected to further processing. HF typically containing up to about 5% of water may be removed continuously or discontinuously from the bottom of the distillation zone. Initially, the bulk liquid used for effecting dehydration of the gaseous product stream in the distillation zone may consist of substantially pure HF but it will be appreciated that, as the process proceeds, the composition of the bulk liquid will gradually change and will comprise primarily HF plus small amounts of water and other components of the gaseous product stream, such as organics and HCl.

The materials of construction used for the distillation zone and which come into contact with both HF and moisture may comprise suitably resistant materials known in the art. Conventional materials of construction can be used for subsequent processing of the dry HF and organics.

Whilst the distillation zone may be constructed using suitably resistant materials, it is preferred that the distillation is constituted by a containment vessel as defined below, which is designed for chemically corrosive fluids at high temperature.

Thus, according to another aspect of the present invention there is provided a containment vessel for chemically corrosive fluid at high temperature, comprising:

an outer shell fabricated from metal which is vulnerable to attack by said fluid;

is a lining of membrane material located adjacent the inner face of the shell and which, over a limited temperature range, is chemically resistant to said fluid;

a tubular column located within, and spaced from, the internal surface(s) of the shell and fabricated from material which is chemically resistant to said fluid over a wider range of temperature than said membrane material, said lining being provided within the gap between the column and the shell;

means for introducing the fluid at high temperature into the interior of the column;

means for effecting cooling of the shell, or the shell being exposed for cooling by ambient air, to create a temperature differential between the interior of the column and the internal face of the shell; and at least one thermal insulation gap provided between the column and the lining to prevent exposure of the lining to temperatures in excess of said limited range.

Preferably the lining of membrane material in addition to providing a chemical barrier to said fluid serves as an insulating material.

By these means, the metal shell is protected against attack by the corrosive fluid.

Preferably the lining is attached to the shell without the use of fittings which penetrate the lining. In a preferred embodiment of the invention the lining is held against the shell by pressure and, to enhance this, a vacuum is conveniently applied between the lining and the internal face of the shell. In this way, the lining is urged against the shell by the pressure differential prevailing on its opposite faces; in practice, the corrosive fluid will usually be at high pressure. Alternatively, the lining may be secured to the shell by adhesive.

The lining is preferably impermeable with respect to the corrosive fluid. However, it is not necessarily essential for it to be totally impermeable; in practice, some degree of permeability may be tolerable since any fluid permeating into the interface region between the shell and the lining may be evacuated from this region.

The lining material will usually be of an organic nature such as PTFE, PFA (polyfluoroalkoxy resin) or PVDF (polyvinylidene fluoride).

The tubular column is typically fabricated from an inorganic material having good temperature and chemical resistance properties, for example, graphite, carbon or carbon fibre compositions. The inorganic material may be fabricated as rings, blocks or bricks and the tubular column assembled therefrom.

The material from which the tubular column is fabricated may be of a porous nature such that the corrosive fluid can permeate the same and enter the insulation gap between the tubular column and the lining. In this event, it will be appreciated that the corrosive fluid occupying the gap may function as an insulant protecting the lining from the high temperatures prevailing within the tubular column. Where the corrosive fluid is employed in this way, preferably provision is made of means for rendering the fluid within the gap substantially static, for example by limiting natural circulation or flow of the corrosive fluid within the gap, so that the heat transfer properties of the corrosive fluid are attenuated. For instance, the gap may be partitioned in the axial direction relative to the tubular column so that fluid entering the gap is confined to a limited axial region and is rendered substantially static. Such partitioning may be effected by means of radial seals between the external periphery of the tubular column and the lining.

Where the tubular column is fabricated from rings, bricks, blocks or the like, compressible seals are conveniently provided between adjacent courses and the column is subjected to compressive loading in order to place the seals under compression thereby preventing or limiting egress of the corrosive fluid at the interfaces between adjacent courses.

The vessel preferably functions to quench the temperature of the incoming high temperature fluid by contacting the same with liquid. A typical application of the invention is in the quenching of process gases consisting of a number of components in such a way as to separate more volatile components from those which are less volatile. Thus, the invention may be in the form of a distillation column, in which case the tubular column will enclose some form of mass transfer packing or internals such as liquid-gas contacting trays or plates. Advantageously, the tubular column serves to mount the packing or column internals.

In one specific application of the invention the corrosive fluid to be handled by the vessel comprises a process gas containing water vapour and HF. As discussed previously, the presence of water in a gaseous process stream containing HF represents a serious obstacle to handling of the process stream because of the highly corrosive nature of condensate containing water and HF. Aqueous solutions of HF attack all normal materials of construction; consequently, unless the problem posed by the presence of water in a process stream which also contains HF can be overcome, expensive HF-resistant coatings have to employed in the fabrication of ductwork, vessels and the like.

According to another aspect of the invention there is provided plant for carrying out a fluorination process involving the generation of a process gas containing HF and water, said plant comprising:

reactor means for effecting gaseous phase reaction of a compound to be fluorinated with HF in the presence of a fluorination catalyst, the reactor means producing a gaseous product stream containing a fluorinated product together with water and HF;

a vessel as defined in said one aspect of the invention and arranged to function as a distillation vessel;

means for introducing said product stream into the interior of said tubular column of the vessel;

means for supplying liquid HF to the tubular column;

fluid-fluid contacting means within the tubular column for effecting fluid-fluid contact between the product stream and the liquid HF thereby reducing the temperature of the product stream while removing a substantial proportion of the water contained in the product stream; and means for feeding the substantially water-free product stream downstream of the vessel.

The liquid HF supplied to the tubular column may be pure HF or it may be a mixture containing HF. For instance, the HF-containing liquid may also contain an organic component or components compatible with the process. In a preferred embodiment of the invention, the HF-containing liquid may be derived from condensation of the vapour phase resulting from distillation of the gaseous product stream and typically contains HF and organics, the HF and organics being re-introduced as a reflux stream into the vessel.

The liquid HF may be supplied to the vessel in the form of more than one stream and, where more than one stream of liquid HF is employed, the different streams may be derived from different sources. For instance, one stream may take the form of a reflux stream from a condenser for condensing HF/organics containing vapour produced in the distillation process, and a second stream may be derived from recycling of HF collecting in the base of the vessel; if desired, the recycled HF stream derived from the base of the vessel may be obtained from downstream distillation of the HF/contaminants collecting in the base of the vessel.

If desired, the insulation between the interior of the tubular column and the lining may be enhanced by the provision of a further gas gap; for instance, the vessel construction may comprise a second tubular column enclosing the first mentioned column and fabricated from material which exhibits chemical resistance over a wider range of temperatures than the lining, the first and second columns being spaced from one another so as to define a first gas gap forming a thermal insulation barrier and the second column being spaced from the lining so as to define a second gas gap also forming a thermal insulation barrier.

The material from which the tubular columns are fabricated may be of a porous nature such that the corrosive fluid can permeate the same and enter the insulation gap between the second tubular column and the lining. In this way, the corrosive fluid may occupy both the gas gap between the two columns and also the gas gap between the second column and the lining and thereby act as an insulant in both gas gaps.

Preferably provision is made of means for limiting circulation or flow of the corrosive fluid within the gap between the first and second columns and also within the gap between the second column and the lining and each gap may be partitioned in the axial direction relative to the tubular columns so that fluid entering each gap is confined to a limited axial region. Such partitioning may be effected for instance by means of radial seals extending between the radial boundaries of each gap.

As in the case of the first tubular column, the second tubular column is conveniently fabricated from rings, bricks, blocks or the like.

In some instances, where at least one gas gap is provided, in operation of the vessel the fluid may undergo a change from the gaseous/vapour phase to the liquid phase and the corrosive liquid may permeate into the gas gap especially in the lower regions of the vessel. In this event, the insulation properties of the liquid will be considerably reduced. Accordingly, where such a change of phase may occur, the gas gap (or at least one of the gas gaps where more than one is present) contains a layer of insulating material extending over at least that region of the vessel where the liquid phase of the corrosive fluid may collect and penetrate into the gas gap(s). For example, the layer of insulating material may comprise a tubular shroud accomodated within the gas gap and may comprise carbon foam, PTFE or PFA material.

Where the corrosive fluid comprises a mixture of HF and water, the lining material is conveniently such that if it is fluid-permeable to any extent, it is selectively permeable towards the HF so that any fluid permeating through the lining is freed of its water content at least to some extent thereby reducing its corrosivity relative to the metal shell.

The vessel and plant of the invention are particularly suitable for operation with a low inventory of HF for the reasons mentioned previously.

Yet another aspect of the invention is concerned with the manner of effecting control of the process for effecting separation of water from a gaseous stream containing inter alia water and HF by contacting the gaseous stream with liquid HF.

According to a this aspect of the invention there is provided a method of treating a gaseous stream containing inter alia water and HF, said method comprising:

contacting the gaseous stream with liquid HF within a distillation zone whereby mass transfer of water to the liquid HF takes place, the water-containing liquid being collected in a sump;

condensing the light ends resulting from the distillation process to derive a liquid stream of HF;

returning the so derived liquid HF as a reflux stream to the distillation zone for contact with the gaseous stream; and controlling said reflux stream to maintain a supply of liquid HF in excess of that necessary to separate a substantial proportion of the water from the gaseous product stream.

Also according to this aspect of the invention there is provided a method of reducing the water content of a hot gaseous product stream containing inter alia HF and water, said method comprising:

contacting the gaseous product stream with liquid HF in a distillation column so as to quench the hot product stream and effect mass exchange between the liquid HF and the gaseous product stream whereby a substantial part of the water content of the latter is separated from the gaseous product stream and constitutes a heavy component of the distillation process;

deriving at least part of the liquid HF from condensation of the light ends of the distillation process and recycling it to the distillation column as a reflux stream such that the liquid HF supplied to the distillation column comprises an amount sufficient to separate substantially all of the water content in the product stream;

collecting the excess liquid HF in a sump at the base of the distillation column;

withdrawing liquid from the sump at a predetermined rate;

monitoring the quantity of liquid in the sump; and controlling the reflux stream to maintain said quantity substantially constant.

A convenient way of monitoring of the quantity of liquid in the sump is by monitoring of the liquid level directly or indirectly.

In this manner, it is possible to ensure removal of a substantial part of the water content of the gaseous product stream even in circumstances where it is not possible to monitor changes in the composition of the gaseous product stream reliably by measurement of temperature within the distillation column, for instance, because of temperature changes in the gaseous product stream and temperature fluctuations in the liquid at the base of the distillation column resulting from variations in the water content of the gaseous product stream. A feature of the invention is that the inventory of HF needed in the column is desirably small since a small volume of liquid in the sump is more sensitive to variations in the reflux liquid flow reaching the sump.

According to yet another aspect of the invention there is provided a distillation plant for reducing the water content of a hot gaseous product stream containing inter alia HF and water, said plant comprising:

a vessel having a fluid-fluid contacting zone;

means for supplying the gaseous product stream to said zone for contact with liquid HF so as to quench the hot product stream and effect mass exchange between the liquid HF and the gaseous product stream whereby a substantial part of the water content of the latter is separated from the gaseous product stream and constitutes a heavy component of the distillation process;

means for condensing the light ends obtained from the fluid-fluid contacting zone to produce a condensate containing HF intially present in the gaseous product stream;

reflux means for supplying at least part of the liquid HF resulting from condensation of said light ends as a reflux stream to said fluid-fluid contacting means such that the liquid HF supplied to said zone comprises an amount sufficient to separate substantially all of the water content in the product stream;

a sump for collecting the excess liquid HF and separated water;

means for withdrawing liquid from the sump at a predetermined rate;

means for monitoring the quantity of liquid in the sump (eg by monitoring the liquid level within the sump directly or indirectly; and means for controlling the reflux stream to maintain said quantity substantially constant.

The liquid HF supplied to the fluid-fluid contacting means may be derived solely from the reflux means. Alternatively the liquid HF supplied to the fluid-fluid contacting means may be derived from more than one source; for instance, the liquid HF supply means may be constituted by the reflux means and a further source or sources such as a recycled flow of HF derived from said means for withdrawing liquid from the sump (eg after distillation of the liquid to separate HF from water).

According to a more specific aspect of the present invention there is provided a process for the manufacture of 1,1,1,2-tetrafluoroethane, comprising:

(a) effecting the gaseous phase reaction of trichloroethylene and/or 1,1,1-trifluoro-2-chloroethane with a stoichiometric excess of HF in the presence of a fluorination catalyst;

(b) contacting the resulting gaseous product stream with liquid HF in accordance with the method according to said first or second aspect of the invention to effect mass transfer of water present in the gaseous product stream to said liquid HF; and (c) recycling HF obtained from said product stream following step (b) to the reaction of step (a).

Where the gaseous stream is introduced at a point above the liquid level as discussed previously, the quantity of liquid in the sump is conveniently monitored directly by monitoring the liquid level directly. Where the gaseous product stream is desuperheated by initially contacting it with the body of liquid in the sump below the level thereof, the quantity of liquid HF in the sump may be monitored by monitoring the liquid level indirectly by establishing a substantially quiescent column of liquid (ie. undisturbed by the gaseous product stream) and monitoring the level of that column to provide a measure of the quantity of liquid forming the sump.

In fluorination reactions of the type with which certain aspects of the present invention are concerned, the reactor system is operated in different regimes. In particular, as well as fluorination, the reactor system may be operated in catalyst regeneration and prefluorination regimes (described hereinafter) accompanied by generation of water in the presence of hydrogen fluoride. Especially in the case of catalyst regeneration, to reduce downtime of the reactor system, it is advantageous to carry out regeneration in a manner involving feeding HF (as a diluent) through the reactor system in much greater quantities than are used during the fluorination process. This gives rise to the problem of handling much larger volumes of water-containing HF than are encountered in the fluorination process. The problem is readily amenable to solution by feeding the HF/water-containing off-gases to a disposal plant for neutralisation or, where the HF is to be recovered for recycling through the reactor system, by designing a water removal distillation column which is sized for the regeneration regime and is substantially larger than needed for water separation during the fluorination process. Such approaches however involve substantial capital costs and, in the case of disposal, result in waste of raw materials.

According to a yet further aspect of the invention there is provided a process for the separation of water from an off-gas derived from a fluorination reactor system when operating in a catalyst regeneration regime, which off-gas contains water and HF, said process comprising:

cooling the off-gas to produce a first liquid phase fraction containing HF/water and a second vapour phase fraction which contains HF and is substantially free of water;

effecting azeotropic distillation of said first fraction to produce HF which is substantially free of water;

subjecting the second fraction to further cooling to condense HF therefrom; and recycling water-free HF derived from both fractions to the reactor system.

Stated more specifically this aspect of the invention resides in a process for effecting fluorination by means of vapour phase HF in the presence of catalyst which requires oxidation treatment in order to regenerate the catalyst and wherein oxidation of the catalyst is accompanied by production of water, said method comprising the following phases of operation:

Phase I (a) passing HF through a fluorination reactor system containing the catalyst for vapour phase reaction with a compound to be fluorinated to produce a gaseous product stream containing inter alia fluorinated product, HF and water;

(b) contacting the product stream with liquid HF to separate from the product stream a first component comprising gaseous HF and a second component comprising HF/water azeotrope;

(c) recycling said first component to the fluorination reactor system;

(d) supplying the second component to means for separating at least some of the HF from the second component;

(e) using HF derived from step (d) in the liquid phase for effecting the contacting step (b);

Phase II (f) discontinuing the fluorination process of Phase I;

(g) supplying a gaseous regeneration stream comprising an oxidising agent and gaseous HF to the fluorination reactor system in order to regenerate the catalyst with the consequent production of a gaseous water-containing stream which also contains HF, the amount of HF so supplied per unit time being greater than that used in step (a);

(h) cooling said water-containing stream sufficiently to produce a first stream containing HF and substantially all of the water and a second gaseous, substantially water-free HF-containing stream;

(i) supplying said first stream to said separating means used in step (d) of Phase I to separate at least some of the HF from said first stream; and (j) recycling HF derived from step (i) and from said second water-free stream to the reactor system together with further oxidising agent.

In this manner, it is possible employ an azeotropic distillation column which is sized for the fluorination process in the regeneration process even when the latter is carried out using a substantially greater throughput of HF. This aspect of the invention is based on the recognition that, because water tends to form a higher boiling point azeotrope with HF, it is possible to remove virtually all of the water constituent from the, off-gas obtained from the reactor system during regeneration by cooling to a temperature at which the HF/water mixture condenses. The remaining vapour phase contains a substantial amount of HF and is virtually free of water; it can therefore be subjected to further cooling to recover the HF as a liquid and the HF so recovered may be used directly for recycle without having to be subjected to a water-HF separation process.

Usually the amount of HF supplied to the reactor system per unit time during Phase II will exceed that supplied during phase I by at least 50%, and often the excess will be at least 100% and may even be greater than 200% and as much as 400% or more.

BRIEF DESCRIPTION OF THE DRAWINGS

In order to illustrate the invention further by way of example only, reference is now made to the accompanying drawings showing different features of plant for the production of HFA 134a (1,1,1,2-tetrafluoroethane).

Figure 1:
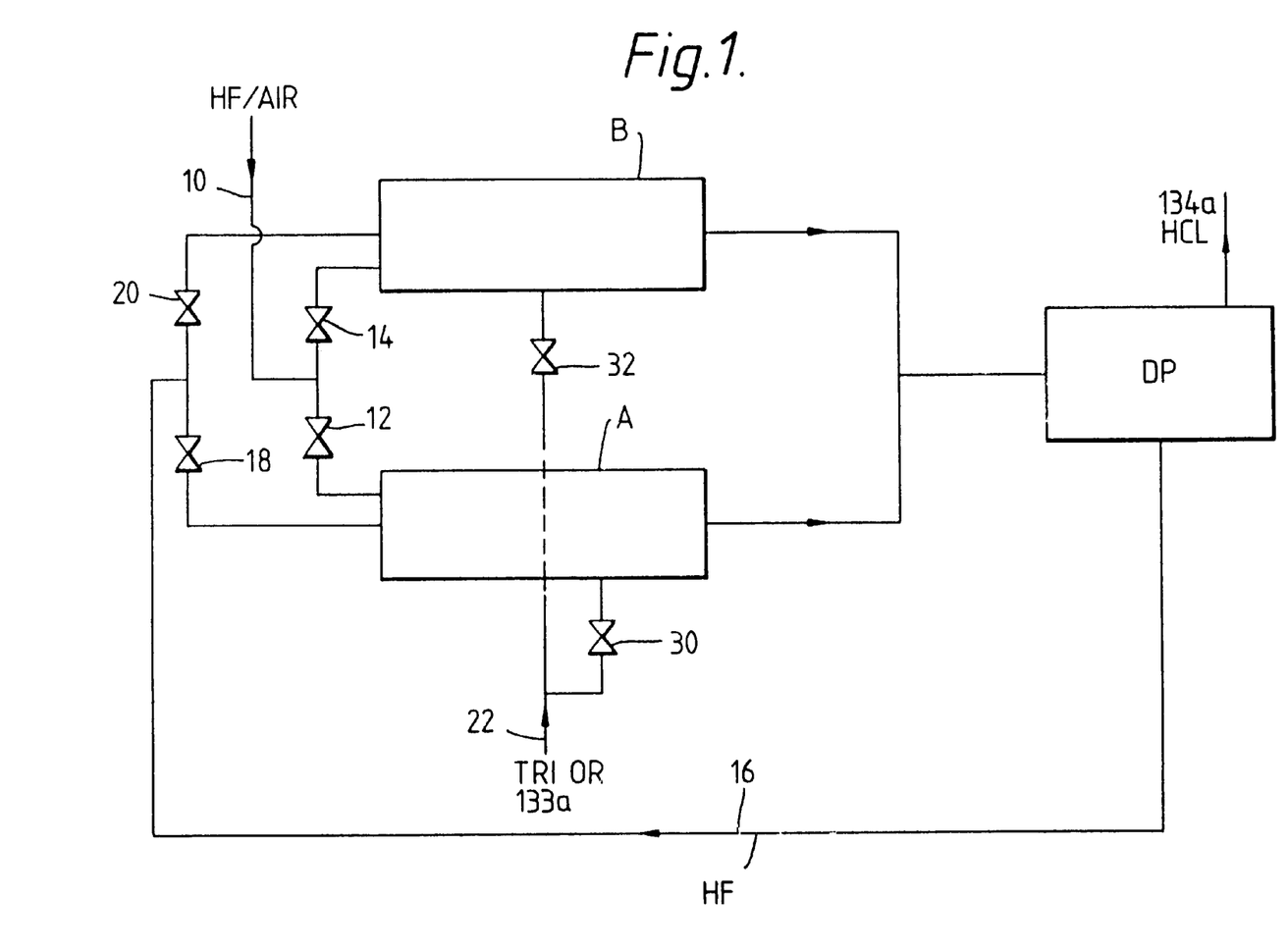
FIG. 1 is a schematic view showing the layout of one form of plant to which the present invention has application.

Referring to FIG. 1, the plant comprises two reactor systems A and B each of which is designed to carry out the fluorination of 133a in a single stage process, or trichloroethylene and/or 1,1,1,-trifluoro-2-chloroethane (133a) in a two stage process as disclosed in for example EP-A-449617. Each reactor system A, B is designed to effect reaction of HF with trichloroethylene and/or 133a depending on the particular design of the reactor system in the presence of a fluorination catalyst, eg chromia. Dry HF (with air) is supplied to the reactor systems via feedline 10 and valve arrangements 12, 14. HF is also supplied (together with 133a and unreacted trichloroethylene in the case of a two stage process as disclosed in EP-A-449617) via a recycle stream 16 and valve arrangements 18, 20 which allow the recycle stream to be fed selectively to one or other of the reactor systems A, B. Trichloroethylene or 133a is introduced via line 28 and valve arrangements 30, 32.

The product stream from reactor systems A, B typically contains 133a, 134a, HCl, unreacted trichloroethylene (if initially present as a reactant) and HF and is fed to downstream processing plant DP in which the product stream is treated to remove water and is then subjected to separation processes to separate 134a and HCl from 133a, HF and any unreacted trichlorethylene, at least the HF (usually HF with trichloroethylene and/or 133a) being recycled to the reactor systems A, B via recycle stream 16. Removal of water is effected by contact of the gaseous product stream with liquid HF as disclosed hereinafter.

In operation, while one of the reactor systems, eg A, is operating in the 134a producing mode, the other reactor system may be operated in a catalyst conditioning or regeneration mode. Thus, where system A is operating in the 134a producing mode, the valve arrangements 18 and 30 are open whilst valve arrangements 20 and 32 are closed. Supply of substantially dry HF to the reactor systems A, B is effected via line 10 and valve arrangements 12, 14, the HF being supplied together with air. When reactor system A is in the 134a producing mode, valve arrangements 14 and 12 are respectively open and closed so that the HF supply to the reactor system operating in the 134a producing mode is supplied with HF via the other reactor system.

When operating in the regenerating mode for example, the HF/air supply from line 10 is admitted into the reactor system, eg B, for contact with the catalyst typically at a temperature in the range of 300 to 500° C., more preferably 330 to 450° C. The reaction with the catalyst results in the production of water (in the gas phase) and wet HF emerges from reactor system B. The off-gases from the conditioning/regeneration process, containing wet HF, are fed to the downstream processing system DP so that the water content can be substantially eliminated. The dry HF is subsequently recycled back to the other reactor via stream 16. It will be seen that in this embodiment, the HF used as a reactant in the 134a producing mode is supplied to the corresponding reactor system after passage through the system operating in the conditioning/regenerating mode.

When the reactor system operating in the 134a producing mode requires regeneration, the functions of the two reactor systems A and B are interchanged by changing over the conditions of the valve arrangements 12/14, 18/20 and 30/32 thus bringing system B onto line for 134a production and placing system A into catalyst regeneration mode.

Figures 2, 3, 4:
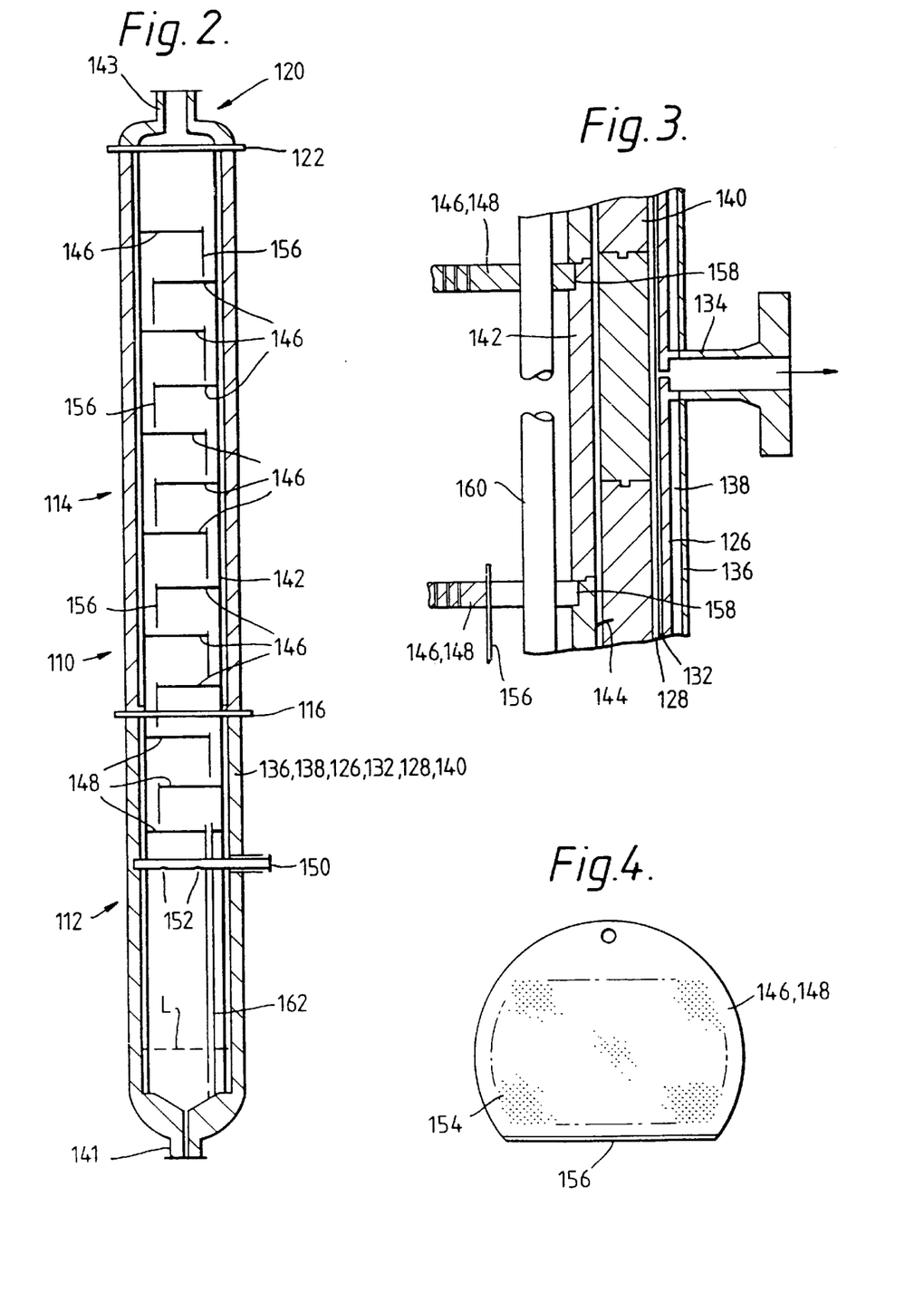
FIG. 2 is a diagrammatic longitudinal section through a containment vessel suitable for use in effecting separation of water from a hot gaseous process stream containing inter alia water and hydrogen fluoride.
FIG. 3 is a fragmentary radial sectional view showing the wall structure of the vessel.
FIG. 4 is a plan view showing one of the sieve trays located within the vessel.

Referring to FIGS. 2 and 3, the vessel shown is intended for quenching a process gas at high temperature and high pressure derived from a fluorination process while effecting separation of water from the process gas. For example, the process gas may comprise the high temperature gaseous/vapour phase stream resulting from a process such as that described above in connection with FIG. 1 involving the reaction of HF with chlorinated alkanes or chlorinated olefines in the presence of a catalyst such as chromium oxide. A typical gaseous/vapour phase product stream is at a temperature of up to about 300° C. and contains fluorinated product, unchanged organic starting material, unchanged HF, hydrogen chloride as a product of the halogen exchange reaction and water vapour, the water vapour typically being present in an amount ranging from about 200 ppm up to about 6000 ppm (relative to the HF). A serious obstacle to the further treatment of this reaction stream is the highly corrosive nature of the condensate because of the presence of moisture together with HF and HCl. The purpose of the vessel shown in FIG. 2 is to quench the process stream as well as remove substantially all of the water content of the stream so that the stream can thereafter be processed further without having to employ special and expensive corrosion resistant materials that would otherwise be necessary if the process stream contains water and HF/HCl.

The vessel is intended to be operated at a pressure of typically between 1 and 15 bara and comprises a vertically disposed elongated unit 110 comprising a lower section 112 and an upper section 114 mounted on the lower section 112 by mating flanges depicted by reference numeral 116 which are bolted together with a suitable sealing arrangement clamped between the faces of the flanges 116 to provide a secure seal capable of withstanding the pressures prevailing within the vessel in operation. The upper section 114 is surmounted by a cover section 120 which is secured to the upper section via mating flanges 122 and bolts, with a high pressure sealing arrangement between the flanges 122. Each section 112, 114 and the cover section 120 comprises a relatively thick metal shell 126 (see FIG. 3) fabricated from a material, such as Inconel 600, which though susceptible to attack by the corrosive HF/moisture mixture if exposed thereto, tends to fail by pinhole development so that, in the event of a failure, only limited leakage can occur initially thus allowing adequate time in which to detect failure and take appropriate action such as shut-down of the plant.

The shell 126 is to a large measure protected from exposure to the hot process stream within the vessel by a lining 128 (see FIG. 3) in the form of an organic membrane layer which is chemically resistant to HF/water, at least when exposed thereto at temperatures below about 150° C. The lining 128 may be fabricated from PTFE or from a perfluoroalkoxy resin. The lining 128 is not bonded to the shell 126; instead it is draped over the internal face of the shell and is urged against the shell by the pressure exerted by the process gas. Between the shell 126 and the lining 128, a layer 132 of gas permeable material is provided which serves to space the lining 128 from the shell 126. The layer 132 is for example in the form of a mesh which allows gas to flow in a direction perpendicular to the thickness of the layer 132. The mesh may for instance be fabricated from PVDF. Means is provided at suitable locations along the height of the unit 110 for evacuating gas within the space afforded by the mesh layer 132; such means are illustrated in FIG. 3 and take the form of conduits 134 penetrating the shell 126, the conduits being connected to one or more vacuum pumps (not shown). The evacuation of the region lying between the lining 128 and the shell 126 serves to withdraw any process gas that may permeate through to this region and also serves to enhance the pressure differential which urges the lining 128 against the shell 126.

The shell 126 of each section 112, 114 and 120 is provided with a jacket 136 which may be of carbon steel and forms a gap 138 through which coolant, eg water, is circulated from one end of the vessel to the other, the inlets and outlets for supply and discharge of the coolant and also interconnecting unions for interconnecting the jacket associated with one section 112, 114, 120 to the jacket associated with an adjacent section being unshown. Inboard of the membrane lining 128, each section 112, 114 and 120 is provided with a temperature resistant lining 140 fabricated from a suitable material such as graphite, carbon or a carbon fibre composition. A suitable material is a porous unfilled graphite such as that marketed under the trade name DIABON OS2 by Sigri GmbH of Germany. The material forming the lining 140 may be in the form of rings, bricks, blocks or the like assembled to form a column, the outer surface of which is spaced from the interior of the shell 126 by a gap in excess of the combined thicknesses of the membrane lining 128 and the mesh material 132. The interfaces between adjacent rings etc of the lining 140 are sealed, for example by suitable temperature resistant jointing cement or grouting materials. In this way, a gas space is provided between the membrane lining 128 and the column formed by the lining 140, which gas space acts as an insulation barrier and also affords clearance for installation of the graphite.

Inboard of the column 140, the lower and upper sections 112 and 114 are provided with an inner column 142 of temperature resistant material. The column 142 may also be fabricated from bricks, rings, blocks or the like of graphite, carbon or a carbon fibre composition, DIABON OS2 again being a suitable material. The inner column 142 is spaced from the outer column 140 by a gap of about 10 mm to afford a gas gap forming an insulation barrier which typically produces a temperature differential of about 80° C. In operation, this gap will normally contain the chemical composition being handled, either in gaseous or liquid form depending on the location along the length of the vessel. In those locations where the chemical composition is likely to exist in the liquid phase and hence deleteriously affects the insulation properties of the gap, a layer of insulating material such as PTFE or PFA of suitable thickness is installed in the gap in order to provide adequate insulation. This layer of insulating material will usually be located in the lower section of the vessel where the chemical composition is more likely to be in the liquid phase. The layer is conveniently loosely draped within the gap by being suspended from suitable supports provided on the inner column 142 and/or outer column 140.

Where the gap between the inner and outer columns 142 and 140 contains gas, usually the chemical composition in its gaseous phase, insulation is more effective if the gas is in a static condition. To achieve this, the gap is partitioned axially of the vessel into sections of about 1 metre by sealing rings 144 which bridge the space between the columns. The seals may be composed of PTFE. These partitioned sections of the gap are each vented, for example by means of holes drilled into for example the inner column so as to accommodate condensation and pressure fluctuation, the holes being positioned to minimise liquid and gas bypassing. Usually the inner column is the thinner of the two columns 140 and 142 and, and in addition to defining the gas gap along with the outer column, serves to provide a support system for the mass/heat transfer internals of the vessel and may also support the insulating lining at those locations where the chemical composition is likely to exist in its liquid phase.

The heat/mass transfer internals in the illustrated embodiment comprise sieve trays organised into two series, namely trays 146 forming a predominantly mass transfer function and trays 148 forming a predominantly heat exchange function so as to desuperheat the incoming process gas stream entering via inlet tube 150 which extends generally horizontally and is formed with a number of downwardly presented openings 152 through which the process gas is discharged in a downwards direction into the vessel above the normal level of the liquid (predominantly HF) within the base of the vessel.

A typical sieve tray 146, 148 is shown in FIG. 4 and may be fabricated from graphite such as that manufactured and sold under the brand name DIABON OS2. As is usual, each sieve tray 146, 148 is formed with orifices 154 over a substantial part of its area to allow gas/vapour to pass upwardly through the sieve plates and contact liquid that collects on the sieve plates. The liquid overflows the sieve trays along a cut-away edge thereof at which a downcomer plate 156 is located so that the overflowing liquid travels downwardly along each downcomer plate 156 for collection on the sieve tray below. The lowest sieve tray 148 is not cut-away and provided with a downcomer plate; instead liquid collecting on the lowest sieve tray is transferred to the body of liquid held in the base of the vessel by a tube 162 so that the liquid is not allowed to stream down the inner surface of the inner column 142 in this region. The column 142 is at its highest temperature in the region adjacent the process gas inlet tube 150 and it is therefore desirable to avoid thermal shock as a result of relatively cool liquid from the lowest sieve tray contacting the hot inner column in this region.

The sieve trays 146, 148 are supported in generally horizontal, vertically spaced apart relation by the inner column 142, the periphery of the plates 146, 148 seating on rebated sections 158 formed in the parts, eg rings, from which the inner column is fabricated (see FIG. 3) with the cut-away edges of the plates 146, 148 spaced from the inner column. The sieve plates 146 and that part of the inner column 142 located within the upper section 114 of the column are assembled as a unit held together by a pair of axially extending tie rods 160 (not shown in FIG. 3) located at diametrally opposite locations, so that the assembly can be installed as a unit by lowering it through the top of the upper section during fabrication of the vessel. The rods 160 may be in the form of tubes fabricated from carbon fibre reinforced carbon. The sieve plates and the downcomer plates may likewise be fabricated from carbon fibre reinforced carbon.

The inner and outer columns are assembled with suitable compressible seals at the joints between the parts from which they are fabricated and the cover section 120 is assembled so as to place each column 140, 142 in compression and thereby compress the sealing arrangements to seal each column along its entire length thereby substantially eliminating any by-passing of the sieve trays 146, 148. The seals employed may be of any suitable temperature and chemically resistant material, such as that sold under the brand name SIGRAFLEX by Sigri GmbH of Germany.

The base of the vessel is similarly lined with an outer membrane layer of PFA, an adjacent intermediate and inner layers of temperature resistant material such as graphite sold under the brand name DIABON OS2. The base of the vessel is provided with an outlet 141 through which liquid can be withdrawn continuously or periodically (as required) for separation of water and other contaminants from HF. After such separation has been effected, the HF can be returned to the vessel, the rate of withdrawal and return being controlled so as to maintain a substantially constant inventory of HF within the vessel. The recycled HF is re-introduced as a liquid stream into the vessel at a location above the bottom three sieve trays 148 so that the process gas contacts liquid HF in this region of the vessel and undergoes substantial reduction in temperature. The heat input provided to the vessel by the incoming process gas allows the distillation process to be operated without the need for a reboiler.

The cover section 120 is provided with an outlet 143 through which the gaseous distillation products exit the vessel and are fed to a condenser (not shown). The vessel is operated so that the distillate exiting via outlet 143 is freed of water that was present in the gaseous product stream as a result of mass transfer between the water vapour-containing gaseous product stream and the liquid HF, the water being removed at least to an extent such that any water present will not, in combination with HF in the distillate, present corrosion problems in downstream processing plant. Usually a water content of less than 200 ppm will be acceptable. Part of the condensed liquid from the condenser is returned to the top of the vessel as a reflux stream containing HF and organics present in the gaseous product stream supplied to the vessel via the inlet 150. The reflux stream returned to the vessel descends the column and undergoes mass and heat transfer contact with the rising water vapour-containing gaseous product stream within the vessel.

In operation, the vessel is operated with a quantity of liquid HF in the base thereof, the normal operating level being indicated by reference L in FIG. 2 and the HF-containing reflux returned to the vessel is supplied in an amount such that there is a net flow of liquid to the base of the vessel, the majority of the reflux being evaporated in the course of descending the trayed section of the vessel. Because of the manner in which the vessel is protected against corrosion by the HF/water component of the gas stream (ie by means of the membrane lining 128, the temperature resistant columns 140, 142 and the insulating gaps), the incoming process gas may be de-superheated by contact with liquid HF on the trayed section comprising trays 148. In this manner, the vessel can be operated with a relatively small inventory of liquid HF which is advantageous from a safety standpoint. The liquid and gas/vapour taking part in the distillation process are substantially confined to the interior of the column 142 by virtue of compressive sealing of the joints in its construction. However, some process liquid/vapour will penetrate the column 142 and also the column 140 by virtue of the porous nature of the material from which they are fabricated. Such liquid/gas will consequently enter the gaps existing between the columns 140 and 142 and between the column 140 and the lining 128. Over the major part of the vessel, the process fluid will be in the gaseous phase and will therefore act as a gaseous insulant in the aforementioned gaps and, because it is rendered substantially static by the partitioning seals 144, it thereby serves to introduce substantial temperature drops in the radial direction towards the lining 128 so that any exposure of the latter to the process fluid only occurs at temperatures that do not result in unacceptable degradation of the lining material.

In the lower regions of the vessel, the process fluid may be cooled to such an extent that it is present as liquid in the gaps and hence its thermal insulation properties will be relatively poor. As previously mentioned, the vessel is provided with layers of insulating material, such as PTFE or PFA, within the gaps in the lower regions of the vessel, to provide the temperature drop necessary to allow the membrane lining 128 to function without becoming degraded. Ideally the membrane lining itself should be impermeable; however, some degree of permeability may be acceptable if the extent to which the water can penetrate past the lining 128 is limited. PFA for instance is permeable to HF to a greater extent than it is to water. Any HF and/or water penetrating the lining 128 may be removed in the course of evacuating the space between the lining 128 and the shell 126.

It is important that the vessel is operated in such a way that all of the water is prevented from passing over the top and thereby causing corrosion problems in downstream processing equipment. Separation of the water component from the incoming process stream is therefore required to be effected within the vessel. It is not readily feasible to use a temperature measurement to infer the composition within the vessel since the incoming gaseous product stream is unlikely to remain fixed and the temperature at the bottom of the vessel can be expected to vary according to the amount of water present in the incoming product stream. To ensure that substantially all of the water is removed, a suitable technique is therefore needed.

As mentioned previously, the arrangement is such that the bottom three trays 148 are effective to remove the superheat from the incoming product stream. This is achieved by evaporation of the majority of the reflux supplied to the vessel. Sufficient trays are provided above the lower trays 148 to ensure good separation, provided sufficient reflux is supplied. If these trays are operating ineffectively, the temperature up the vessel will rise significantly. This will occur if there is insufficient reflux to the vessel. Under normal conditions, excess reflux is supplied with the aim of ensuring that a predetermined net flow of liquid enters the base of the vessel. A corresponding amount of liquid is withdrawn from the base of the vessel so that, provided that the predetermined net flow of reflux liquid flow to the vessel base is maintained, the level in the vessel base remains constant. If the liquid reflux flow to the vessel base is reduced, it will be appreciated that the liquid level will fall. Thus, by monitoring the liquid level within the vessel base, variation in the liquid level can be compensated for by controlling the reflux supplied to the vessel from the condenser. In operation, the water within the vessel will constitute a heavy end of the distillation process and will therefore tend to collect in the vessel base. However, the amount of water present in the volume of liquid HF at the base will not be sufficient to cause significant changes in the liquid level. From the foregoing, it will be seen that a small control volume of liquid in the base is desirable in order to permit rapid response of the level to variations in the reflux flow. A small control volume of liquid in the vessel also results in operation of the distillation column with a small inventory of HF which is advantageous from the safety standpoint.

In the illustrated embodiment, the shell 126 is shown enclosed within a water cooling jacket 136. However, alternative means for effecting cooling of the shell may be employed; for example, instead of a water jacket, the shell may be provided with a so-called limpet coil comprising ducting wound around the shell in spiral fashion with coolant circulated through the ducting to cool the shell and hence create a temperature gradient such that the membrane lining is not exposed to temperatures exceeding its operating limit. In another alternative embodiment, the shell may be cooled by ambient air.

Although the illustrated embodiment has two columns of temperature resistant material and hence two gaps for insulant gas, it is within the scope of the invention to use a single column of temperature resistant material. For instance, in an alternative embodiment, the columns 140, 142 may be replaced by a single column of graphite forming an insulating gap between itself and the membrane lining. In this event, the single column may additionally serve to support the internals such a sieve trays or other heat and mass transfer packing.

Figure 5:
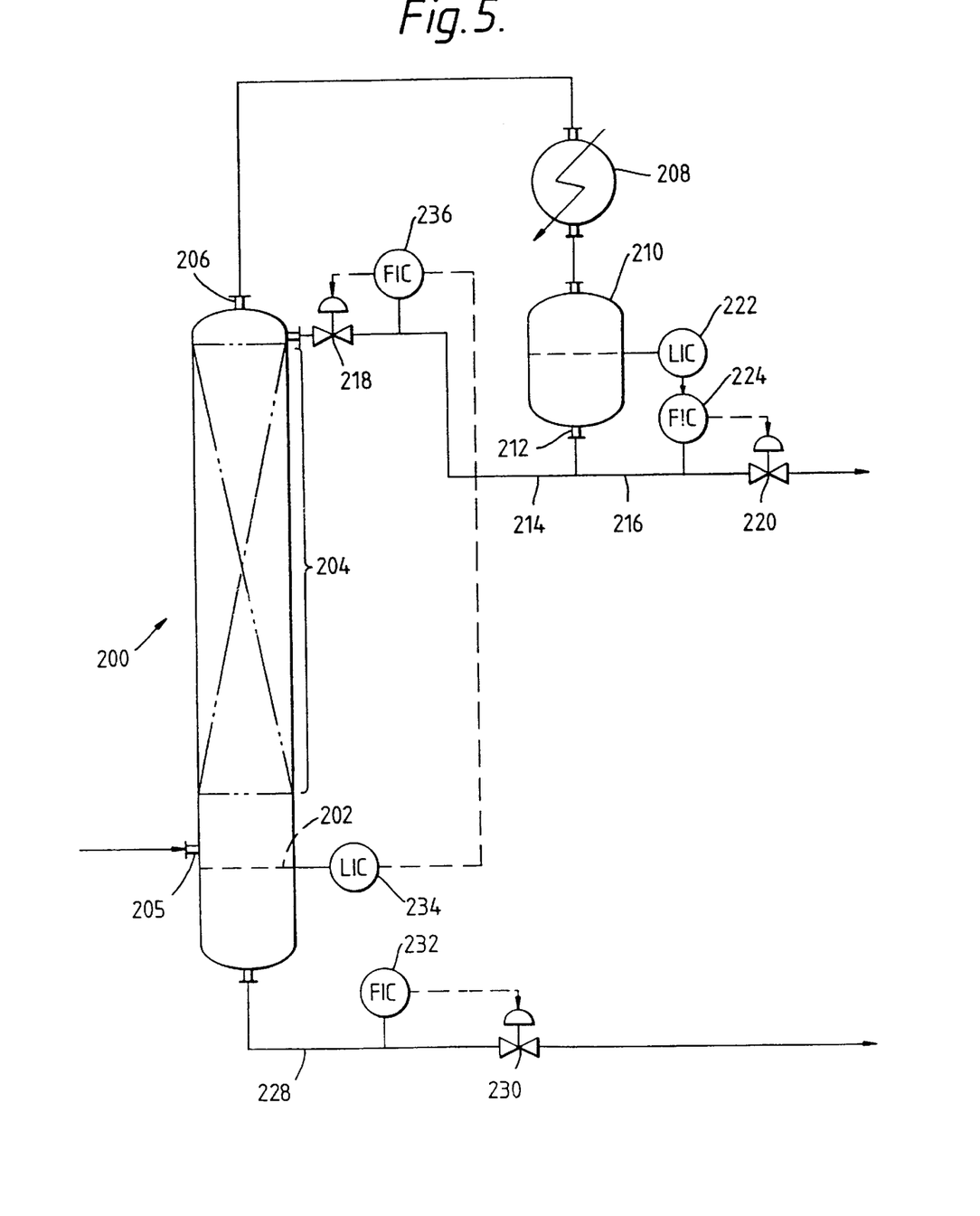
FIG. 5 is a schematic view of a distillation column which may be of the form shown in FIGS. 2 to 4 and is provided with a control system in accordance with the invention.

Referring now to FIG. 5, the downstream processing plant includes, inter alia, a distillation column 200 such as that described above in relation to FIGS. 2 to 4. The base of the column 200 in normal operation forms a sump containing a quantity of liquid which is predominantly HF but also includes a small amount of water and organics separated out in the course of the distillation process. The level of the liquid in the sump is depicted by reference numeral 202. Above the sump, the column is provided with a fluid-fluid contacting zone 204 which may comprise a conventional column packing or may be trayed; for the purposes of the present description, it will be assumed that the contacting zone is formed by a series of vertically spaced sieve trays and associated downcomers as described in relation to the column of FIGS. 2 to 4. The hot gaseous HF/water containing stream produced by upstream plant, such as that described in relation to FIG. 1 or as described hereinafter, is introduced into the column 200 at a location 205 above the liquid level 202 and below the lowermost tray of the contacting section 204. The relatively high temperature of the incoming gaseous stream enables the column to be operated without the need for a reboiler.

The hot incoming gaseous stream is initially quenched by contact with liquid HF over a lower de-superheating zone of the trayed section 204, constituted for example by the three lowermost sieve trays of section 204. The remaining sieve trays forming the contacting section 204 primarily serve to enhance mass transfer between the rising gaseous stream and a falling stream of liquid consisting mainly of HF, the liquid HF being derived at least in part from condensation of the condensible components contained in the gaseous/vapor stream exiting the upper end of the distillation column via outlet 206.

The stream exiting at outlet 206 is passed to a condenser system 208 and the condensed components, including HF and organic components (inter alia 134a), are collected in pot 210, the outlet 212 of which feeds reflux line 214 and a downstream line 216 respectively controlled by valves 218 and 220. The liquid level within the pot 210 is controlled by a level controller 222 which manipulates the liquid distillate flow via a flow controller 224 associated with valve 220, level controller 222 and flow controller 224 forming a cascaded loop enabling the effects of secondary disturbances, such as pressure drop fluctuations across valve 220, to be removed. The liquid distillate routed via valve 220 is subjected to further processing culminating in the isolation of the desired end product, 134a. The reflux stream comprising substantially dry HF and organics is fed via valve 218 into the distillation column at a point above the contacting section 204 and undergoes mass transfer with the rising gaseous stream and also serves to effect quenching of the hot incoming gaseous stream over the de-superheating zone formed by the lowermost sieve trays of contacting section 204.

It is important that the column is operated in such a way that all of the water is prevented from passing over the top and thereby causing corrosion problems in downstream processing equipment. Separation of the water component from the incoming process stream is therefore required to be effected within the column. It is not readily feasible to use a temperature measurement to infer the composition within the column since the incoming gaseous product stream is unlikely to remain fixed and the temperature at the bottom of the column can be expected to vary according to the amount of water present in the incoming product stream. To ensure that substantially all of the water is removed, a suitable technique is therefore needed.

As mentioned previously, the arrangement is such that the lowermost sieve trays are effective to remove the superheat from the incoming product stream. This is achieved by evaporation of the majority of the reflux supplied to the column. Sufficient trays are provided above the lowermost trays to ensure good separation, provided sufficient reflux is supplied. If these trays are operating ineffectively, the temperature up the column will rise significantly. This will occur if there is insufficient reflux to the column. Under normal conditions, sufficient reflux is supplied with the aim of ensuring that a predetermined net flow of liquid (derived from the reflux and any other source of liquid HF supplied to the column for effecting water removal) enters the base or sump of the column. A corresponding amount of liquid is withdrawn from the base of the column via line 228 and valve 230 (controlled by flow controller 232) so that, provided that the predetermined net flow of reflux liquid flow to the column base is maintained, the level in the column base remains constant.

If the liquid reflux flow to the column base is reduced, it will be appreciated that the liquid level will fall. Thus, by monitoring the liquid level within the column base by means of level controller 234 (which is arranged in a cascaded loop with the controller 236 associated with valve 218 to remove secondary disturbances, such as pressure drop fluctuation across valve 218), variation in the liquid level can be compensated for by controlling the valve 218 and hence the reflux supplied to the column from the condenser system. In operation, the water within the column will constitute a heavy component of the distillation process and will therefore tend to collect in the column sump. In practice, the amount of water present in the volume of liquid HF at the base will not be sufficient to cause significant changes in the liquid level. From the foregoing, it will be seen that a small control volume of liquid in the base is desirable in order to permit rapid response of the level to variations in the reflux flow. A small control volume of liquid in the column also results in operation of the distillation column with a small inventory of HF which is advantageous from the safey standpoint.

The liquid removed from the sump or base of the vessel via the line 228 in practice will comprise mainly HF with a small quantity of water and organics present also. This liquid, as mentioned above, is drawn off at a predetermined rate and may be fed to a still in order to separate the different constituents. At least part of the substantially dry HF recovered in this way may be returned to the distillation column to supplement the substantially dry HF provided by the reflux stream from the condenser system.

Figure 6:
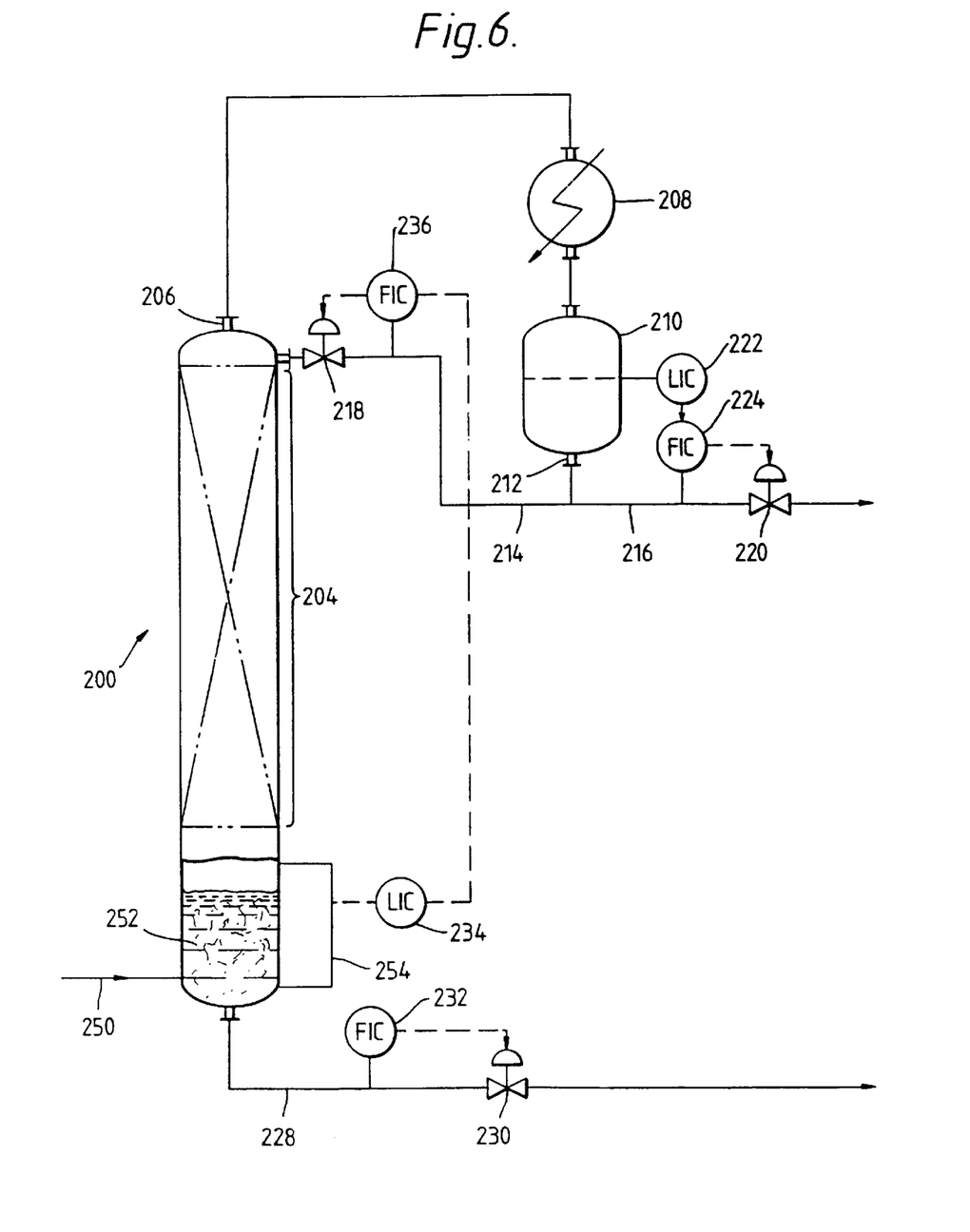
FIG. 6 is a view similar to that of FIG. 5 but showing a modified form of column, like parts being identified by the same reference numerals in FIGS. 5 and 6.

Referring now to FIG. 6 which shows a distillation column which may be identical to that of FIG. 5 in all respects except for the mode of introducing the gaseous product stream into the column. In this case, the hot product stream is quenched by introducing it via inlet 250 into the body of liquid 252 (primarily liquid HF) at the base of the column. The product stream bubbles to the surface and then passes up through the gas-liquid contacting section 204 which, as in the case of FIG. 5, may be formed by a column packing or a series of trays and associated downcomers. Again the reflux stream derived from the condenser 210 is supplied in an amount which ensures that substantially none of the water present in the incoming gaseous product stream goes over the top, and the reflux stream is controlled so as to maintain a substantially constant volume of liquid at the base of the column in the same way as described with reference to the embodiment of FIG. 5. However, in this case, because the liquid level is disturbed by bubbling of the product stream, the quantity of liquid at the base of the column is monitored and maintained constant by tapping off liquid from this region into a generally vertically disposed conduit 254, the bottom end of which communicates with the liquid and the top end of which communicates with the interior of the column at a point above the liquid level at the base. In this way, a substantially quiescent column of liquid is established in the conduit 254, the height of the liquid column providing a measure of the amount of liquid present at the base. The level of the liquid column in the branch conduit 254 is monitored, by level controller 234 which, in conjunction with the cascaded flow controller 236, allows the reflux flow via valve 218 to be regulated so as to maintain the quantity of liquid in the base of the column substantially constant thereby ensuring that an excess of liquid HF is supplied to the column to effect removal of substantially all of the water in the product stream.

Figure 7:
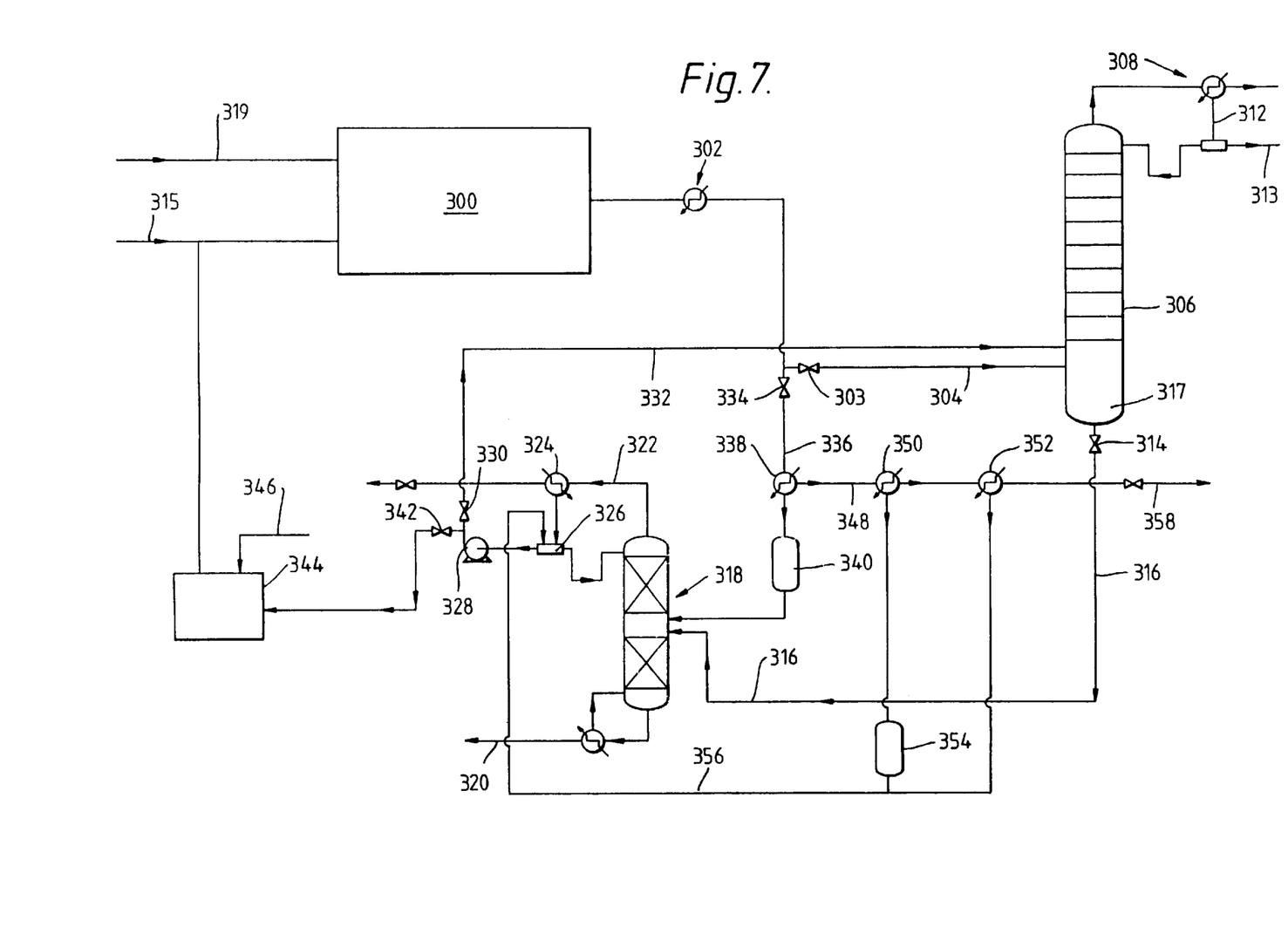
FIG. 7 is a flow diagram showing the circulation of hydrogen fluoride in a plant for carrying out fluorination of a compound using hydrogen fluoride.

Referring to FIG. 7, the plant illustrated comprises at least one reactor system 300 such as that depicted by reference A or B described in relation to FIG. 1 in which fluorination is carried out using a catalyst of the type which needs to be subjected to a regeneration process in the course of which process water is generated in the presence of HF, the HF being used as a diluent during the regeneration of the deactivated catalyst. In the regeneration process, air may be used to regenerate the catalyst in order to burn carbon which deposits on the catalyst surface in the course of the fluorination process and which tends to deactivate the catalyst. The regeneration process is exothermic and, in order to limit the exotherm and hence prevent undesirable effects such as damage to the catalyst, HF is used as a diluent.

During the regeneration process, the volume of HF passing through the reactor system 300 may be considerably larger than that passing through the reactor system during the fluorination process, especially when rapid regeneration is required so as to limit downtime of the reactor system. For instance, during regeneration the volume of HF passing through the reactor system may typically be of the order of four times greater than during the fluorination process. Moreover the quantity of water that evolves may be substantial compared with the initial stages of the fluorination process. The problem therefore arises of dealing with the large quantities of water-containing HF that leave the reactor system 300.

During the fluorination process, the HF/water is combined with the gaseous product stream which is fed via aftercooler 302, valve 303 and line 304 to a distillation column 306 such as that described with reference to FIGS. 2 to 4 equipped with a condensing system 308 from which a vapour product stream 310 and a liquid HF stream 312 are derived. The latter is partly returned as a reflux to the distillation column 306 in the manner described with reference to FIGS. 5 and 6 while the remainder is recycled via lines 313 and 315 to the reactor system, the recycled HF being vaporised and re-introduced into the reactor system together with make-up HF, the total HF input to the reactor system being preheated. In the column 306, water is separated from the product stream by contact with liquid HF and collects in the sump 317 along with liquid HF and other heavy constituents derived from the product stream. The liquid in the sump is fed via valve 314 and line 316 to a distillation column 318 where azeotropic distillation is carried out resulting in a bottoms product comprising water/HF azeotrope and a substantially pure HF top product respectively withdrawn via lines 320 and 322. The HF top product is condensed in condenser 324 and collects in condensate pot 326 from which it is fed by pump 328 via valve 330 and line 332 to the column 306 for contact with the product stream entering via line 304.

During the regeneration process, pre-heated HF is supplied to the reactor system 300 together with air supplied via line 319 for burning off carbon accumulated on the catalyst, the HF acting as a diluent. The off-gas from the reactor system consists primarily of HF but will also contain components such as unreacted nitrogen from the air, unreacted oxygen (the amount of which increases since lesser amounts of $O_2$ will react as regeneration proceeds), products of reaction such as CO, $CO_2$, and $H_2O$. The off-gas passes through the after-cooler 302 where it is cooled to within about 30° C. of the dew point and, instead of passing to the distillation column 306 via valve 303, is routed via valve 334 along line 336 to condenser 338 which uses water as the coolant to condense a fraction including substantially all of the water present in the off-gas. The condensed fraction collecting in condensate pot 340 corresponds generally to the amount that the distillation column 318 is designed to handle during the fluorination process. That fraction is then subjected to azeotropic distillation in column 318 to produce a bottoms product which is removed via line 320 and comprises HF/water azeotrope (of reduced quantity compared with the amount present in the off-gas stream) and a top product comprising substantially pure HF which is condensed by condenser 324, collects in pot 326 and is fed by pump 328 via valve 342 to a vaporiser 344 where it is vaporised along with make-up HF supplied via line 346 and recycled to the reactor system 300.

The non-condensed fraction obtained from condenser 338 will contain virtually no water since the water is removed by the condenser 340. The non-condensed fraction contains a substantial amount of HF, generally far in excess of that which could be handled by the column 318 when the latter is designed for handling the amounts of HF/water circulating during the fluorination process. The excess non-condensed HF is fed via line 348 to a further condenser or condensers (two are shown, arranged in series, in the illustrated embodiment) 350 and 352. The condensed fraction obtained from condenser 350, which uses water as the coolant, is collected in condensate pot 354 and will essentially consist of pure HF. Similarly the condensed fraction obtained from condenser 352, which uses a low temperature coolant (typically at −38° C.), essentially consists of pure HF. Both fractions derived from condensers 350 and 352 are fed via line 356 to the pot 326 where they are combined with the condensed top product from the column 318 and then fed to the vaporiser 344 for recycle to the reactor system 300. The non-condensed fraction obtained from condenser 352 will consist mainly of $N_2$, $CO_2$, CO and some HF and is fed via line 358 to for example a thermal oxidiser. The HF lost via line 358 is replaced from the make-up source connected to line 346.

From the foregoing, it will be seen that the substantially larger quantities of water-containing HF employed during the regeneration process can be handled and recycled using an azeotropic still 318 which need only be sized for handling the significantly smaller quantities of HF employed during the fluorination process.

The above described system, namely the HF recovery system formed by the condensers 338, 350 and 352, may also be used during prefluorination of the catalyst using HF. Prefluorination is the name given to the process whereby the catalyst pre-cursor is made active. During prefluorination, HF is absorbed on to the surface of the catalyst followed by bulk incorporation of fluoride to produce the active phase. Water is generated in the course of the reactions that take place during prefluorination. The HF used during the prefluorination process may be recovered, and the water generated may be removed, in a similar manner to that described above in relation to regeneration. On completion of the prefluorination process, the reactor system may be cooled to a target temperature suitable for the fluorination process by passing substantially pure HF through the reactor system at a high flow rate. However, during cooling, no significant quantities of water are generated and HF recovery for recycling through the reactor system may be effected using the HF recovery system, possibly just the condenser 338, without using the distillation column 318 since water removal is not needed during the cooling regime. In this event, the HF condensed by the condenser 338 may be routed directly to the pot 326 without passing through the column 318.

What is claimed is:

1. In a process comprising:
   effecting gaseous phase reaction of an organic compound selected from the group consisting of chlorinated alkanes and chlorinated olefines, with a stoichiometric excess of HF in the presence of a fluorination catalyst to produce a gaseous product stream containing a fluorinated organic compound, excess HF and water, the improvement which comprises:
   (a) contacting the resulting gaseous product stream containing fluorinated organic compound, excess HF and water and having a temperature above the dew point of the HF/water component in said gaseous product stream and in the range of 150° C. to 300° C., with liquid HF to effect mass transfer of water present in the gaseous product stream to said liquid HF and to produce a residual treated gaseous product stream comprising said fluorinated organic compound and HF;
   (b) separating the HF from the fluorinated organic compound of said residual treated gaseous product stream; and
   (c) recycling at least part of the separated HF obtained in step (b) to effect said gaseous phase reaction.

2. A process as claimed in claim 1, wherein part of the HF separated from the fluorinated organic compound is used as the liquid HF in step (a) for effecting removal of water from the gaseous product stream.

3. A process as claimed in claim 1 wherein
   in step (a), said contacting of the gaseous product stream containing the fluorinated organic compound, HF and water with liquid HF is effected within a distillation zone, and the resulting water-containing liquid HF is collected in a sump;
   in step (b), the HF is separated from the fluorinated organic compound by condensing the residual treated gaseous product stream to obtain a liquid stream of HF; and the process further comprising the steps of:
   returning part of the liquid HF obtained in step (b) as a reflux stream to the distillation zone for contacting with the gaseous product stream; and
   controlling said reflux stream to maintain a supply of he liquid HF in said distillation zone in excess of that necessary to separate the water from the gaseous product stream.

4. A process as claimed in claim 1 wherein
   in step (a), said contacting of the gaseous product stream with liquid HF is effected in a distillation column;

in step (b), separating at least part of the HF from the fluorinated organic compound by condensing said residual gaseous product stream to obtain a liquid stream of HF and the process including the further steps of:

recycling the liquid HF obtained in step (b) to the distillation column as a reflux stream such that the liquid HF supplied to the distillation column comprises an amount sufficient to separate substantially all of the water content in the gaseous product stream;

collecting the liquid HF in a sump at the base of the distillation column;

withdrawing the liquid HF from the sump;

monitoring the quantity of the HF liquid in the sump; and controlling the reflux stream to maintain said quantity of the liquid HF in the sump substantially constant.

5. A process as claimed in claim 1 wherein
in step (a), said contacting of the gaseous product stream with said liquid HF is in a fluid-fluid contacting zone;
in step (b), separating the HF from the fluorinated organic compound by condensing the residual treated gaseous product stream to obtain a liquid stream of HF; and
the process further comprising the steps of:
supplying at least part of the liquid HF obtained from step (b) as a reflux stream to said fluid-fluid contacting zone such that the liquid HF supplied to said zone comprises an amount sufficient to separate substantially all of the water content in the gaseous product stream;
collecting the liquid HF and separated water in a collected zone;
withdrawing the liquid HF from the collection zone;
monitoring the quantity of the liquid HF in the collection zone; and
controlling the reflux stream to maintain said quantity substantially constant.

6. A process as claimed in claim 1 in which the water content in the gaseous product stream before the contacting in step (a) is at least 200 ppm relative to the HF in the gaseous product stream.

7. A process as claimed in claim 1, wherein the contact between the gaseous product stream and the liquid HF is effected in a distillation zone with the gaseous product stream at an elevated temperature and pressure so that HF and the product in said gaseous product stream are distilled from the water.

8. A process as claimed in claim 7, wherein the water separated by said distillation is absorbed into said liquid HF which is withdrawn from the distillation zone and subjected to a separation process to effect separation of water from the HF.

9. A process as claimed in claim 8, wherein the gaseous product stream is at an elevated temperature such that reboil heat input to the distillation zone is provided by the gaseous product stream.

10. A process as claimed in claim 7 in which the gaseous product stream or a fraction thereof is introduced into the distillation zone at a point above the HF liquid level.

11. A process as claimed in claim 7 in which the distillation zone includes a series of trays disposed in vertically spaced relation such that liquid HF collects on the trays in the course of the distillation process for contact with the gaseous product stream.

12. A process as claimed in claim 7 in which the gaseous product stream is introduced into the liquid HF at a point beneath the HF liquid level thereof so as to effect de-superheating the incoming gaseous product stream.

13. In a process for effecting fluorination by means of vapour phase HF in the presence of a fluorination catalyst which requires oxidation treatment in order to regenerate the catalyst and wherein oxidation of the catalyst is accompanied by production of water, the improvement which comprises the following phases of operation:

Phase I (a) passing HF through a fluorination reactor system containing the catalyst for vapour phase reaction with a compound to be fluorinated to produce a gaseous product stream containing fluorinated product, HF and water;

(b) contacting the gaseous product stream with liquid HF to separate from the product stream a first component comprising gaseous HF and a second component comprising HF/water azeotrope, wherein said gaseous product stream having a temperature above the dew point of the HF/water component in said gaseous product stream and in the range of 150° C. to 300° C.;

(c) recycling said first component to the fluorination reactor system;

(d) supplying the second component to means for separating at least some of the HF from the second component;

(e) using the HF derived from step (d) in the liquid phase for effecting the contacting step (b);

Phase II (f) discontinuing the fluorination process of Phase I;

(g) supplying a gaseous regeneration stream comprising an oxidising agent and gaseous HF to the fluorination reactor system in order to regenerate the catalyst with consequent production of a gaseous water-containing stream which also contains HF, the amount of gaseous HF supplied per unit time in step (g) being greater than that used in step (a);

(h) cooling said water-containing stream sufficiently to produce a first stream containing HF and substantially all of the water and a second gaseous, substantially water-free HF-containing stream;

(i) supplying said first stream to said separating means used in step (d) of Phase I to separate at least some of the HF from said first stream; and (j) recycling HF derived from step (i) and from said second water-free stream to the reactor system together with further oxidising agent.

14. A process as claimed in claim 13 in which the amount of HF supplied to the reactor system per unit time during Phase II exceeds that supplied during phase I by at least 50%.

* * * * *